United States Patent [19]
Lowne

[11] Patent Number: 5,708,278
[45] Date of Patent: Jan. 13, 1998

[54] REFLECTIVE WETNESS DETECTOR

[75] Inventor: Alan John Lowne, Victor, N.Y.

[73] Assignee: Johnson & Johnson Clinical Diagnostics, Inc., Rochester, N.Y.

[21] Appl. No.: 648,234

[22] Filed: May 13, 1996

[51] Int. Cl.$^6$ .................................................. G01N 21/86
[52] U.S. Cl. ................................ 250/559.4; 250/214 A
[58] Field of Search ......................... 250/559.4, 559.41, 250/559.44, 559.45, 574, 576, 214 R, 214 A, 214 LA, 214 RC, 339.11, 341.8; 356/440, 448, 239, 240, 41; 330/136, 59, 308; 333/14

[56] References Cited

U.S. PATENT DOCUMENTS

| | | | |
|---|---|---|---|
| 3,325,649 | 6/1967 | Bird | 250/219 |
| 3,405,268 | 10/1968 | Brunton | 250/83.3 |
| 3,471,698 | 10/1969 | Mausteller | 250/83.3 |
| 3,522,739 | 8/1970 | Coor et al. | 356/41 |
| 3,773,424 | 11/1973 | Selgin | 356/181 |
| 3,863,071 | 1/1975 | Campanella | 250/339 |
| 3,906,232 | 9/1975 | Meihofer | 250/341 |
| 3,932,133 | 1/1976 | Ishakawa | 23/253 |
| 4,006,358 | 2/1977 | Howarth | 250/339 |
| 4,059,405 | 11/1977 | Sodickson et al. | 23/230 |
| 4,097,743 | 6/1978 | Carlson | 250/339 |
| 4,110,079 | 8/1978 | Schaeffer et al. | 23/253 |
| 4,171,918 | 10/1979 | Mactaggart | 356/408 |
| 4,203,724 | 5/1980 | Sawai et al. | 23/230 |
| 4,224,032 | 9/1980 | Glover et al. | 23/230 |
| 4,243,883 | 1/1981 | Schwarzmann | 250/343 |
| 4,420,566 | 12/1983 | Jessop et al. | 436/46 |
| 4,492,868 | 1/1985 | Jelvestam et al. | 250/345 |
| 4,553,033 | 11/1985 | Hubble | 250/353 |
| 4,655,349 | 4/1987 | Joseph et al. | 356/240 |
| 4,723,554 | 2/1988 | Oman | 128/664 |
| 4,808,824 | 2/1989 | Sinnar | 250/339 |
| 4,840,706 | 6/1989 | Campbell | 162/198 |
| 4,857,735 | 8/1989 | Noller | 250/339 |
| 4,871,917 | 10/1989 | O'Farrell | 250/341 |
| 4,879,471 | 11/1989 | Dahlquist | 250/359.1 |
| 5,017,787 | 5/1991 | Sato | 250/360.1 |
| 5,059,394 | 10/1991 | Phillips | 422/68.1 |
| 5,067,092 | 11/1991 | Hamann | 364/496 |
| 5,084,620 | 1/1992 | Butturini | 250/338.5 |
| 5,508,521 | 4/1996 | Kraft | 250/574 |

FOREIGN PATENT DOCUMENTS

| | | |
|---|---|---|
| 61-173134 | 8/1986 | Japan . |
| 62-025238 | 2/1987 | Japan . |
| 62-254454 | 10/1987 | Japan . |
| 63-149759 | 6/1988 | Japan . |
| 4-248445 | 9/1992 | Japan . |
| 7-012723 | 1/1995 | Japan . |

*Primary Examiner*—Que Le
*Attorney, Agent, or Firm*—Dana M. Schmitt

[57] ABSTRACT

A reflective wetting or spot detecting system incorporates a light emitting diode and a solid state photo sensor arranged on the same side of a medium being analyzed. The sensor is carried at one end of an elongated housing with a linear channel extending through. The channel is oriented on a line that is normal to the medium being analyzed. The channel functions as a lensless, passive focuser of reflected radiant energy. The source of radiant energy is located at an acute angle with respect to the medium. A conditioning circuit is coupled to the output of the sensor. The conditioning circuitry includes a current-to-voltage converter, a signal reducing stage, an amplifying stage and a comparator. The signal reducing stage reduces the voltage signal, produced by the current voltage converter, a predetermined amount, thereby effectively providing the amplifier stage with a greater dynamic range than it would have otherwise had. The output from the amplifier stage charges a capacitor with first and second different time constants depending on whether a medium to be analyzed is present or not. Output from the comparator circuitry drives output amplifiers to provide a digital signal indicative of a wetting or spotting event.

16 Claims, 5 Drawing Sheets

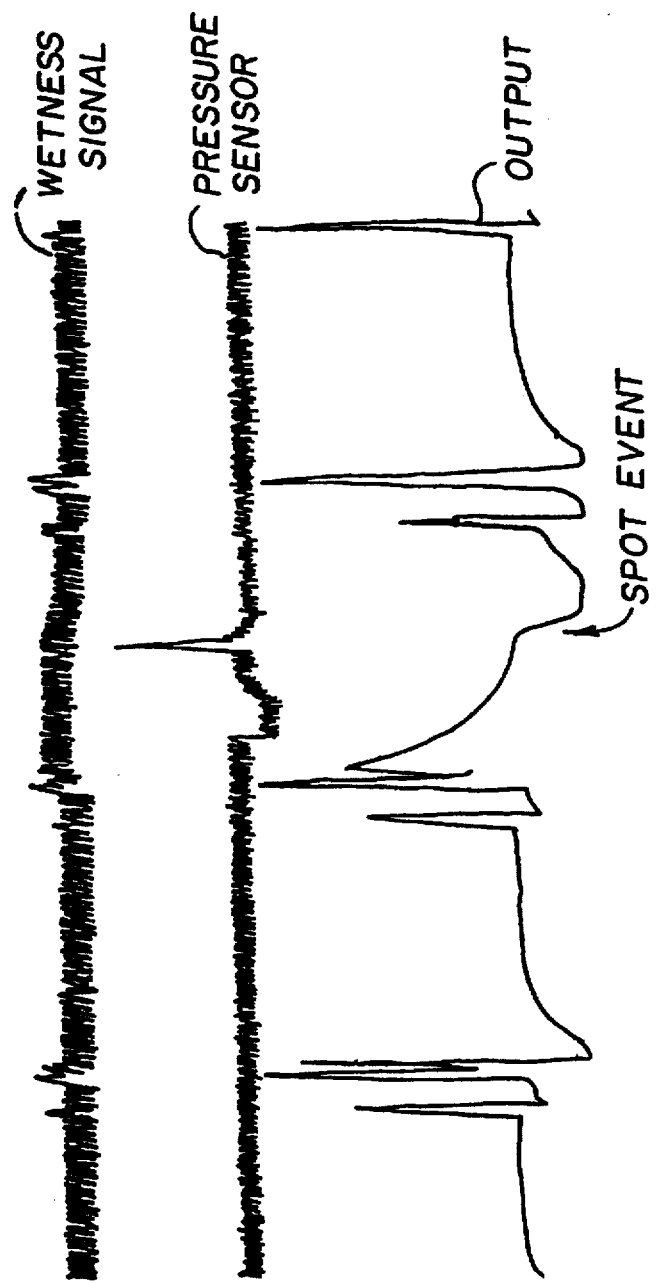

REFLECTIVE WETNESS DETECTOR

FIELD OF THE INVENTION

The invention pertains to circuits for detecting wetting of a medium. More particularly, the invention pertains to such circuits which have solid state sources of radiant energy and solid state detectors which detect radiant energy reflected off a wetted medium.

BACKGROUND OF THE INVENTION

Systems for detecting the presence of a predetermined fluid on a test slide or medium are known. One such system which uses an incandescent light source and which operates in a reflective mode is disclosed in U.S. Pat. No. 4,420,566, entitled "Method and Apparatus for Detecting Sample Fluid on an Analysis Slide". U.S. Pat. No. 5,084,620 entitled "Method of Detecting Pre-Spotting when Dispensing Sample" discloses a transmissive only system which incorporates a solid state source and a solid state sensor disposed on opposite sides of a medium. Both the '566 and the '620 patents have been assigned to the assignee hereof and are incorporated herein by reference.

One known wetness detection scheme uses an incandescent lamp mounted in a molded ramp at 90° to the slide surface and a lead sulfide sensor at 60° which receives light through a glass infra-red filter, see FIG. 1. It is expected that a water absorption band around 1600 nm will be uniform for all chemistry types and produce a sufficient signal for detection. In practice, this system requires careful adjustment of the lamp filament to aim it at the correct location on the underside of the slide.

The incandescent lamp system is hard to adjust, is expensive, and does not work reliably for some chemistry types. The lamp has a field life of only 3–6 months.

The signal produced in the above noted system is relatively small. It would be beneficial if it was larger.

With no slide, the output is approximately 75 mV (see FIG. 2A). When a slide is present, the output increases by 20 mV.

When the slide is spotted, or wetted, indicated by a spike in a fluid dispensing pressure sensor signal (FIG. 2B), the signal decreases by 10 mV. The signal carries at least 10 mV of noise. This signal is passed on to a differential amplifier, with a 100 µF/4.99K time constant.

When a slide enters the wetting position, the differential amplifier receives a positive spike which decays down. A negative transition due to a wetness signal causes the output of this differential amplifier to spike downwards and then recover.

Associated software interprets the downward spike as a valid wetness indicator if it occurs concurrently with the dispense pressure spike,see FIG. 2C. A prespot is reported by the interpreting software if the from ramp slope is less than the slope after the dispense pressure spike. This can occur if the wetness signal is too great, causing the differential amplifier to saturate initially before its exponential decay.

Thus, there continues to be a need for systems and methods of detecting wetting with higher signal levels than known systems. Preferably, a reflectance mode of operation can be used. Also, it would be desirable to use solid state sources of radiant energy and to eliminate false signals due to the arrival of a slide to be analyzed.

SUMMARY OF THE INVENTION

A wetting or spot detecting system in accordance with the present invention, utilizes a light emitting diode in combination with a solid state radiant energy sensor arranged on the same side of a medium being analyzed so as to function in a reflectance mode.

Radiant energy reflected off the medium is convened to a corresponding electrical signal. The electrical signal is processed in an amplifier system which incorporates limiting circuitry. The limiting circuitry in combination with an amplifier circuit provides a broader dynamic range than is possible with just the amplifier circuit alone.

The amplified output is processed in a comparator circuit. One input to the comparator circuit is a reference input which changes in response to first and second RC time constants. Initially, when a medium first moves into position to be analyzed, output from the amplifier circuitry is coupled, via a diode, to a capacitor and to the reference input. Forward biasing the diode causes the capacitor and the reference input to track the input signal closely with a very small time constant.

Subsequently, variations from the amplifier circuitry fall in magnitude and as a result the diode ceases conduction. Consequently, the reference signal changes only slowly as a result of a larger RC time constant. In this mode, a drop in voltage, for example, 300 mV, from the amplifier system which is indicative of detected wetness or spotting, is not great enough to produce an immediate change in the reference signal.

The comparator will then change state from a higher voltage to a lower voltage, on the order of zero volts, indicating the presence of detected wetness or spotting. The low voltage is fed back, via a non-linear feed-back element to the signal input to the comparator, thereby clamping the comparator at a low output state until reset when the slide is removed. It resets quickly as another diode is forward biased when the signal is lower than the capacitor's stored voltage. The low output state can be communicated to further circuitry through a voltage follower or other buffer circuitry.

In one aspect of the present invention, the light emitting diode is oriented at an angle less than 90° to the medium being analyzed. The solid state photosensor is oriented along a line normal to the medium being analyzed.

The photosensor can be positioned in an elongated housing which functions as a form of a passive, lensless focusing device. This produces a narrow viewing angle for the sensor.

In another aspect of the invention, a low passband (780 nm cutoff) filter can be used in the above described system. This passband together with the narrow viewing angle of the sensor means that ambient light has little or no effect on the sensor. As a result, it may be used with the machine covers open.

Numerous other advantages and features of the present invention will become readily apparent from the following detailed description of the invention and the embodiments thereof, from the claims and from the accompanying drawings in which the details of the invention are fully and completely disclosed as a part of this specification.

BRIEF DESCRIPTION OF THE DRAWINGS

FIGS. 2a, 2b and 2c are graphs illustrating outputs from the system of FIG. 1;

DETAILED DESCRIPTION OF THE PREFERRED EMBODIMENTS

Figure 1:
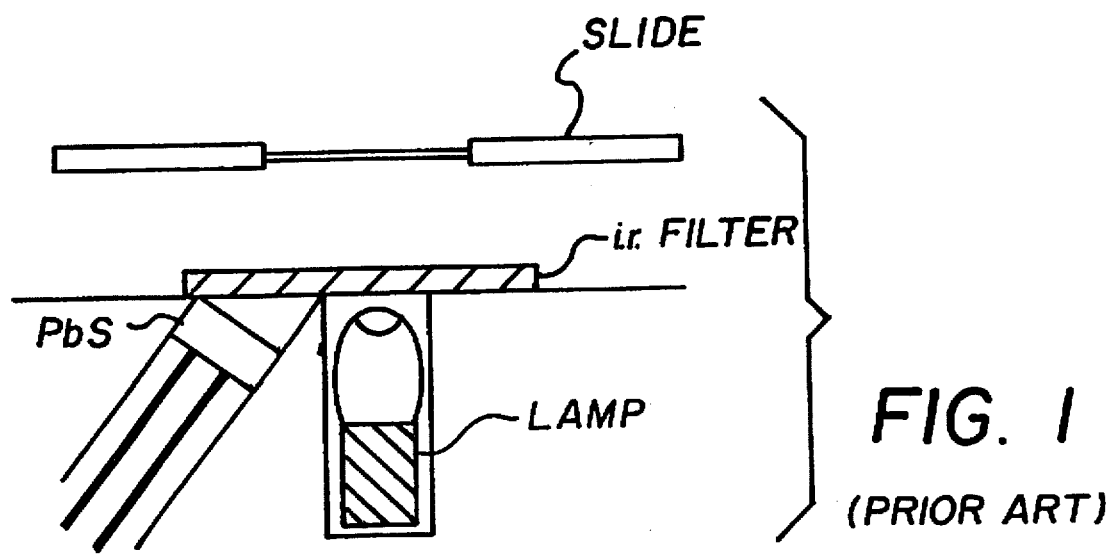
FIG. 1 is a partial, enlarged, side sectional view of a known design of a wetting detection system.

While this invention is susceptible of embodiment in many different forms, there are shown in the drawing and will be described herein in detail specific embodiments thereof with the understanding that the present disclosure is to be considered as an exemplification of the principles of the invention and is not intended to limit the invention to the specific embodiments illustrated.

Figure 3:
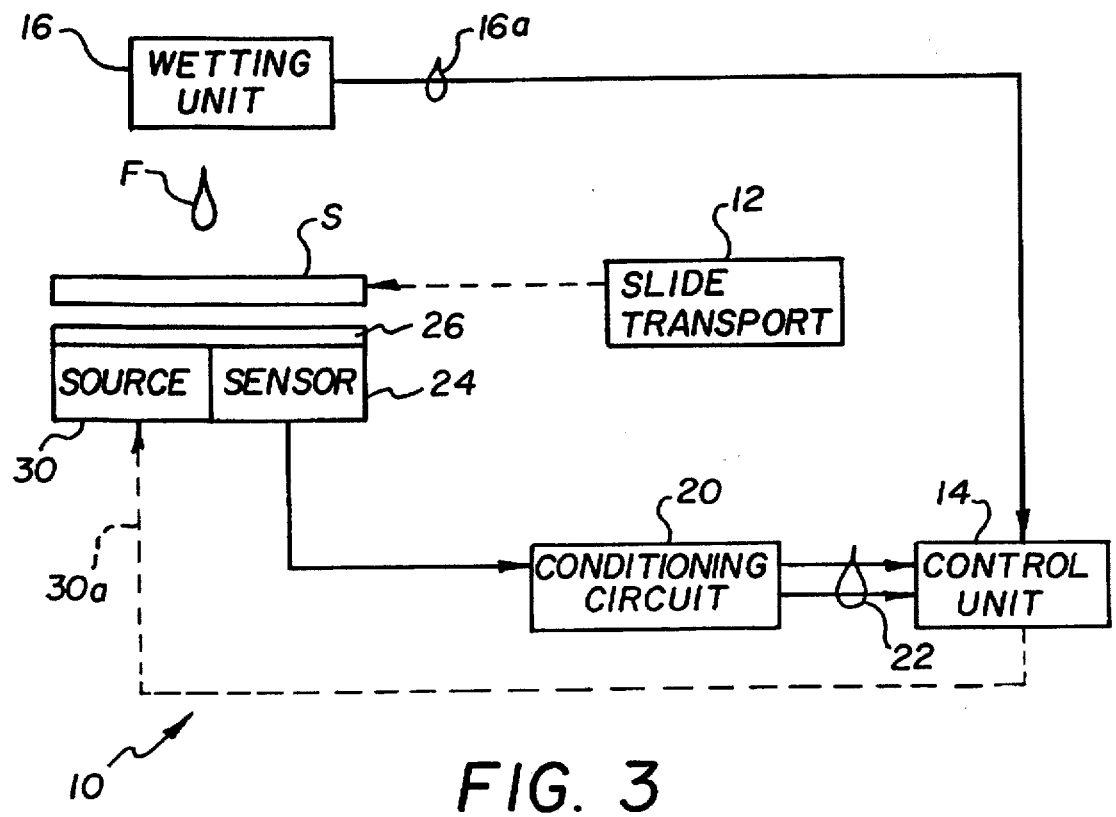
FIG. 3 is a block diagram of a system in accordance with the present invention.

FIG. 3 illustrates a system 10 in accordance with the present invention. The system 10 is used for purposes of analyzing the contents of a slide or medium S which is moved into an analysis position by a conventional slide transport mechanism 12. It will be understood that the mechanism 12 could move the slide linerally or circumferentially without departing from the spirit and scope of the present invention.

Coupled to the slide transport unit 12 is a control unit 14 which could be implemented as hardwired logic. Alternately, the unit 14 could be implemented as a programmed processor, such as a commercially available microprocessor.

The control unit 14 is in turn coupled to a wetting unit 16 which provides one or more drops of a suitable fluid F to the slide S. A pressure sensor in the wetting unit 16 returns a pulse to the control unit 14 on lines 16a indicative of one or more drops of fluid F being dispensed onto the slide S.

Conditioning circuitry 20 is coupled to the control unit 14 and provides signals on lines 22 indicative of the occurrence of a wetting or a spotting event. The conditioning circuits 20 receive signals from a sensor 24 which is configured to receive reflected infrared radiant energy. The reflected radiant energy is received, via a filter 26, from the slide S.

A source of radiant energy 30 is energized by the control unit 14 appropriately to generate a beam of infrared radiant energy which is directed, through the filter 26 toward the slide S to in turn be reflected therefrom to the sensor 24. The source 30 can be continuously energized. Alternately, it could be pulsed by control unit 14 by means of lines 30a, illustrated in phantom.

Figure 4:
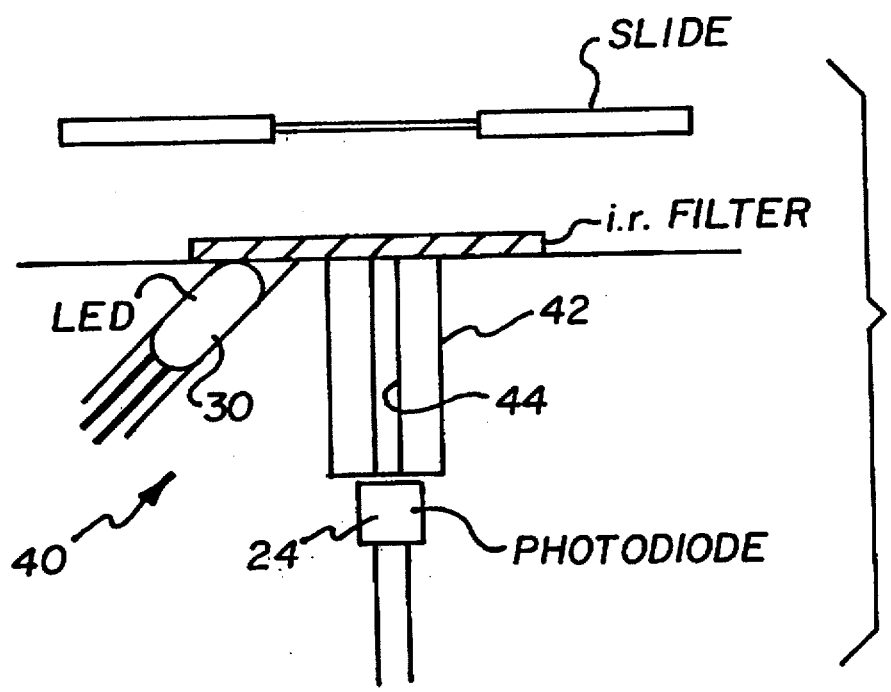
FIG. 4 is an enlarged, partial, side view of a slide sensing station in accordance with the present invention.

FIG. 4 illustrates details of the electromechanical structure of the source 30 and the sensor 24. A molded ramp generally indicated at 40 is used to support the sensor 24 and source 30.

The structure 40 indicates a housing 42 which defines a 10 mm×2 mm diameter bore 44 in front of the sensor or photodiode 24. The bore 44 passively focuses the light beam reflected from the 3 mm center of the slide, without any need for adjustment or lenses, see FIG. 4. It has been found that placing an infrared led source 30 at 60° and the photodiode 24 at 90° to the surface of slide S produces an improved signal compared with the above described known arrangement of FIG. 1 of illuminator at 90° and sensor at 60°. It is possible that a polarization effect is taking place. The area of illumination may be visualized by placing a phosphorescent infrared card at the slide wetting position.

Table 1 illustrates improved output with the sensor 24 in a vertical orientation as in FIG. 4 as opposed to having the source 30 oriented vertically.

TABLE I

| CHEM | VERTICAL LED - V1 | | | | VERTICAL SENSOR - $V_s$ | | | | |
|------|------|------|------|----------|------|------|------|----------|----------|
|      | DRY  | WET  | –δV  | % CHANGE | DRY  | WET  | –δV  | % CHANGE | % Vs > V1 |
| Mg   | 2.00 | 1.90 | 0.10 | 4.93     | 2.045 | 1.875 | 0.17 | 8.28    | 67.9 |
| LAC  | 2.07 | 1.97 | 0.10 | 4.76     | 2.129 | 1.974 | 0.16 | 7.28    | 53.0 |
| GLU  | 2.09 | 1.97 | 0.11 | 5.41     | 2.171 | 1.974 | 0.20 | 9.09    | 68.2 |
| TP   | 1.16 | 0.71 | 0.45 | 39.02    | 1.325 | 0.705 | 0.62 | 46.81   | 19.9 |
| NH3  | 2.27 | 2.12 | 0.16 | 6.83     | 2.143 | 1.946 | 0.20 | 9.21    | 34.8 |
| AST  | 2.20 | 1.61 | 0.59 | 26.92    | 2.059 | 1.382 | 0.68 | 32.88   | 22.1 |
| THEO | 2.20 | 2.16 | 0.04 | 1.92     | 2.030 | 1.904 | 0.13 | 6.25    | 225.0 |
| AMYL | 2.24 | 1.61 | 0.63 | 28.30    | 2.115 | 1.438 | 0.68 | 32.00   | 13.1 |
| BuBc | 2.27 | 2.17 | 0.10 | 4.35     | 2.073 | 1.974 | 0.10 | 4.76    | 9.5 |
| Ca   | 2.26 | 2.17 | 0.08 | 3.75     | 2.129 | 2.002 | 0.13 | 5.96    | 58.9 |
| CHOL | 2.19 | 1.59 | 0.59 | 27.10    | 2.002 | 1.438 | 0.56 | 28.17   | 4.0 |

There is a water absorption band at 935 nm. However, it has been determined that leds that emit at a wavelength of 880 nm or 935 nm give very similar results. This is because the signal-difference is not due to water absorption of light intensity, but due to changes in reflection and transmission between wet and dry slides. The path length is thought to be too small for an absorption effect to be taking place.

Figure 5A:
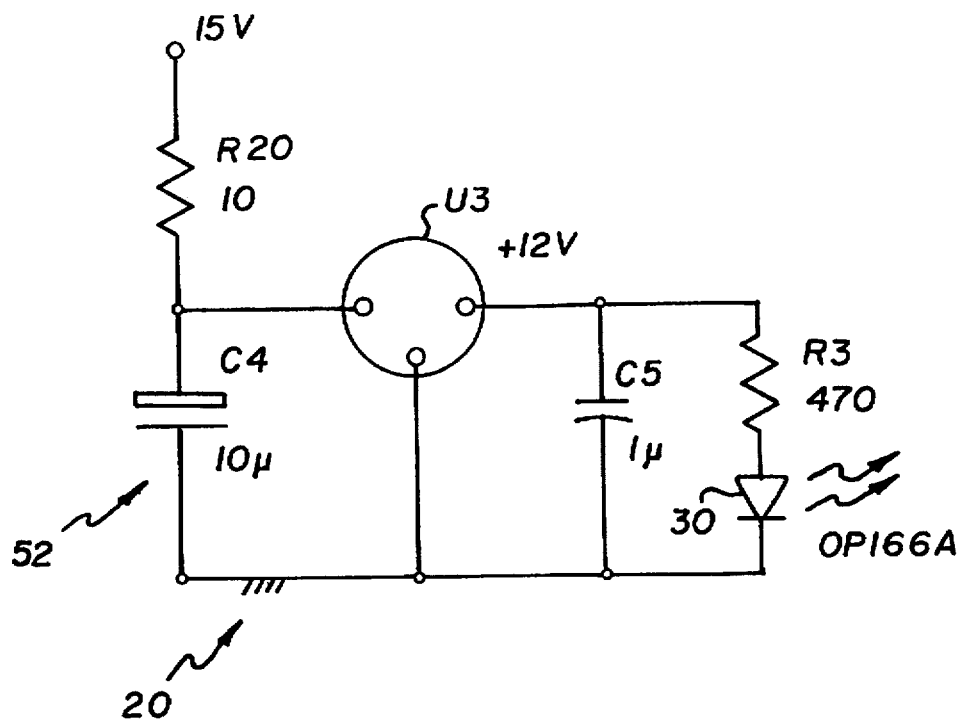
FIG. 5a is a schematic diagram a regulator circuit usable with the system of FIG. 3.

The conditioning circuitry 20 includes, see FIG. 5a, a voltage regulator circuit 52. Circuit 52 includes a regulator U3. Various regulators can be used as would be recognized by one of skill in the art.

Regulator U3 for example, regulates a 15 volt positive supply to 12 volts to remove any adverse effects of supply noise. The light emitting source 30, an Optek OP166A 935 nm led, is continuously driven at 24 mA from 12V through a 470Ω resistor. Although a current driven alternative may offer slightly less led decay, the conditioning circuit 20 has been designated to operate at a 30% reduction of light output. The led 30 could also be driven in a pulsed mode.

Figure 5B:
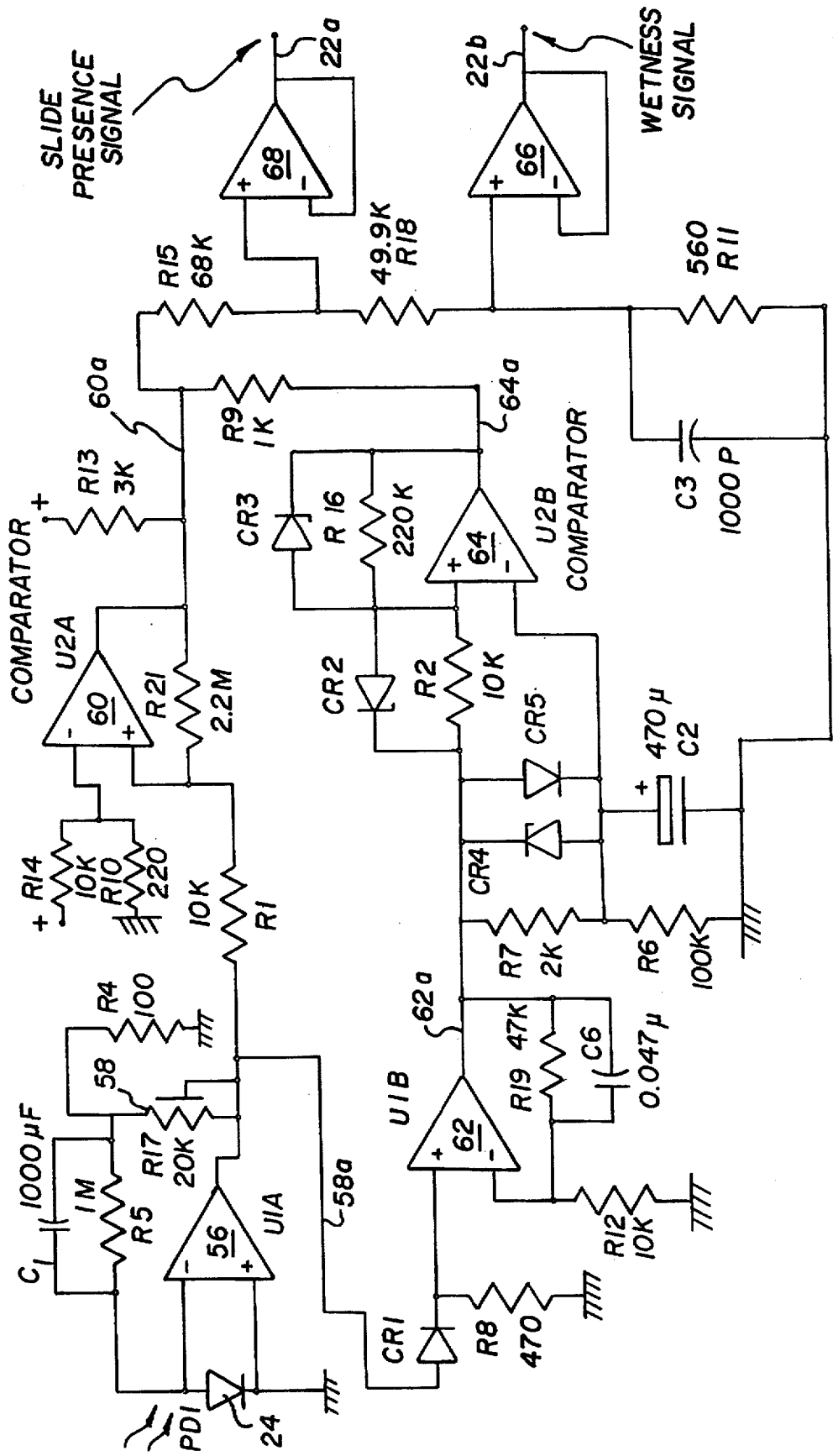
FIG. 5b is a schematic diagram of conditioning circuitry useable with the system of FIG. 3.

With respect to FIG. 5b, a first stage of amplification 56 is a configured as a current-to-voltage converter, giving a voltage output linearly related to the current generated by an OP993 photodiode sensor 24. A potentiometer 58 is located in the feedback loop to compensate for manufacturing variations. The pot 58 is adjusted at manufacture so that a test object produces a 10 volts output at a second stage. (Discussed later).

The effect of resistors R17 and R4 is that of an impedance multiplier. Hence, feedback resistor R5 can be 1Ω lower than otherwise required. The first amplifier 56 is followed by a voltage comparator 60, which increases its output from about zero volts to 12 V on a line 60a in the presence of a slide S.

At an input to a first stage of amplification 62, a silicon diode CR1 is used to drop the signal from current-to-voltage convertor 58, on a line 58a, by about 600 mV in order to improve the signal dynamic range without allowing the signal to go negative as would be the case by simple amplifier subtraction of 0.600 volts (see Table 2).

On Table 2, Column A specifies the chemistry type of a particular specimen to be analyzed. Column B indicates dry readings, due to reflectance off a slide of radiant energy from the source 30, as indicated on the line 58a. Column C indicates the voltage reading on the same line for a wet or spotted slide. Column E indicates the result of amplifying the respective values from Column B by a gain of 4.5. Column F indicates the result of amplifying the respective values from Column C by the same game. Column D indicates the voltage change as the respective slide goes from a wet to a dry condition. Column G indicates the respective percent change.

Column H indicates the results of subtracting 0.6 volts from the values of Column B. Column I represent the results of subtracting 0.6 volts from the values of Column C.

Columns J and K respectively indicate the results of processing respective values of Columns H and I with a gain factor of 6.2. Column L indicates a changing voltage between respective values of Columns J and K. Column M indicates respective percent changes. Column N represents percent improvement in voltage change as a result of the previously noted subtraction process.

promptly respond as soon as a new slide is presented in the wetting or spot position.

A down going wetness signal is generated on a line 64a and on a line 22b when the positive input, of amplifier 64 falls below the negative input thereof. With a slide S present, the positive input sits at 2% less than the signal on line 62a.

The positive input is at CR2's Schottky diode drop above the output on line 64a—about 200 mV—since comparator 64 is normally at 12 V, with a dry slide, pulled up by R9/R13. Schottky diode CR2 is used to ensure that the voltage difference between the comparator inputs is always the same for varying inputs (due to chemistry type or decay of led). With the output line 64a, of comparator 64 at 12 volts, diode CR3 is reverse biased and hence has no effect.

A 300 mV negative change in signal on line 62a from amplifier 62 causes the output of comparator 64 to change state. With the output of comparator 64 now at 0 volts, CR3 turns on and holds the positive input at 200 mV above ground. This ensures that the output on a line 64a remains low, since some chemistries nearly recover to their dry signal value, which would result in a spot error being reported. The signal drop on line 64a to 0 V rams R9/R13 into a voltage divider, and the wetness signal output line 22b is reduced to 10 mV from about 50 mV. It will be understood that different gains and amplifier configurations could be used instead of the illustrated buffer 66 without departing from the spirit and scope of the present invention.

In the present system, the output signal on lines 64a or 22b, is uniform every time for every slide type. (See Table 3 for the otherwise non-uniform response seen at the output of amplifier 62).

TABLE 2

| A | B | C | E × 4.5 AMP | F × 4.5 AMP | D | G | H | I | J × 6.2 AMP | K × 6.2 AMP | L | M | N |
|---|---|---|---|---|---|---|---|---|---|---|---|---|---|
| CHEM | DRY | WET | DRY* | WET* | V CHANGE | % CHANGE | −0.6 V DRY | WET | DRY* | WET* | V CHANGE | % CHANGE | % IMPROVE |
| Mg | 2.17 | 2.00 | 9.79 | 8.98 | −0.81 | −8.28 | 1.58 | 1.39 | 9.77 | 8.65 | −1.12 | −11.43 | 38.10 |
| LAC | 2.26 | 2.1 | 10.19 | 9.45 | −0.74 | −7.28 | 1.66 | 1.50 | 10.32 | 9.30 | −1.02 | −9.91 | 36.04 |
| GLU | 2.31 | 2.1 | 10.39 | 9.45 | −0.94 | −9.09 | 1.71 | 1.50 | 10.60 | 9.30 | −1.30 | −12.28 | 35.09 |
| TP | 1.41 | 0.75 | 6.34 | 3.38 | −2.97 | −46.81 | 0.81 | 0.15 | 5.02 | 0.93 | −4.09 | −81.48 | 74.07 |
| NH3 | 2.28 | 2.07 | 10.26 | 9.31 | −0.95 | −9.21 | 1.68 | 1.47 | 10.42 | 9.11 | −1.30 | −12.50 | 35.71 |
| AST | 2.19 | 1.47 | 9.86 | 6.61 | −3.24 | −32.88 | 1.59 | 0.87 | 9.86 | 5.39 | −4.46 | −45.28 | 37.74 |
| THEO | 2.16 | 2.02 | 9.72 | 9.11 | −0.61 | −6.25 | 1.56 | 1.42 | 9.67 | 8.84 | −0.84 | −8.65 | 38.46 |
| AMYL | 2.25 | 1.53 | 10.12 | 6.88 | −3.24 | −32.00 | 1.65 | 0.93 | 10.23 | 5.77 | −4.46 | −43.64 | 36.36 |
| BuBc | 2.20 | 2.1 | 9.92 | 9.45 | −0.47 | −4.76 | 1.61 | 1.50 | 9.95 | 9.30 | −0.65 | −6.54 | 37.38 |
| Ca | 2.26 | 2.13 | 10.19 | 9.58 | −0.61 | −5.96 | 1.66 | 1.53 | 10.32 | 9.49 | −0.84 | −8.11 | 36.04 |
| CHOL | 2.13 | 1.53 | 9.58 | 6.88 | −2.70 | −28.17 | 1.53 | 0.93 | 9.49 | 5.77 | −3.72 | −39.22 | 39.22 |

As a remit, gain of 4.7 in the stage 62 can be provided to amplify the signal without hitting the rail, or saturating the output, for any chemistries. Rail-to-rail amplifier 62, for example, an LT1014, ensures maximum output excursion on a line 62a before clipping occurs. The resistor potentiometer 58 is adjusted in test to produce 10 volts on the line 62a to ensure that the signal will not hit the rail for all chemistries and will still work when the output of the led 30 decays by 30%.

The signal is then transferred on the line 62a to a voltage comparator 64, which has a time delay of CR5/C2 on its negative input. This ensures that signal bounce on the front edge of the slide S will not cause a wetness signal.

Two diodes CR4/CR5 are used, back-to-back, across resistor R7 to ensure that the capacitor C2 charges and discharges with a short time constant (diodes turn on when the voltage difference across R7 is greater than the diode drop) when a slide S is entering the analysis station. A long time constant (2K/470 µF) is provided when the slide S is in position (diodes off). As a result, the wetness detector will

TABLE 3

| CHEMISTRY | DRY | WET | CHANGE |
|---|---|---|---|
| THEO | 9.03 | 8.30 | 0.73 |
| TBIL | 9.67 | 5.81 | 3.86 |
| Ca | 9.82 | 9.10 | 0.72 |
| Mg | 9.12 | 8.20 | 0.92 |
| CK-MB | 9.74 | 8.60 | 1.14 |
| BUN | 9.23 | 8.60 | 0.63 |
| LAC | 9.57 | 8.70 | 0.87 |
| BuBc | 9.63 | 9.00 | 0.63 |
| AMYL | 9.62 | 5.39 | 4.23 |
| AST/VIS | 9.31 | 5.20 | 4.11 |
| AST | 8.97 | 5.20 | 3.77 |
| Fe | 8.97 | 5.20 | 3.77 |
| Li | 9.35 | 5.30 | 4.05 |
| ECO2 | 9.11 | 7.11 | 2.00 |
| LDH | 4.34 | 1.50 | 2.84 |

TABLE 3-continued

| CHEMISTRY | DRY | WET | CHANGE |
|---|---|---|---|
| GGT | 4.96 | 1.50 | 3.46 |
| ALC | 10.06 | 5.40 | 4.66 |
| DGXN | 4.37 | 0.40 | 3.97 |
| NH3/AMON | 9.96 | 8.80 | 1.16 |
| PHYT | 4.36 | 1.30 | 3.06 |
| CHOL | 8.74 | 5.00 | 3.74 |
| ACP | 9.35 | 5.60 | 3.75 |
| PROT | 6.45 | 3.60 | 2.85 |
| SALI | 9.63 | 8.77 | 0.86 |
| CHE | 9.50 | 5.74 | 3.76 |
| CREA | 9.28 | 8.40 | 0.88 |
| TP | 4.74 | 1.10 | 3.64 |
| TRIG | 9.01 | 8.20 | 0.81 |
| GLU | 9.69 | 8.80 | 0.89 |

The following is an identification of chemistry types from Table 3:

| | |
|---|---|
| THEO | THEOPHYLINE |
| TBIL | TOTAL BILIRUBIN |
| Ca | CALCIUM |
| Mg | MAGNESIUM |
| CK-MB | CREATINE KINASE MB |
| BUN | UREA NITROGEN |
| LAC | LACTATE |
| BuBc | BILIRUBIN UNCONJUGATED/CONJUGATED |
| AMYL | AMYLASE |
| AST/VIS | ASPARTATE AMINOTRANSFERASE (VISIBLE WAVELENGTH) |
| AST | ASPARATE AMINOTRANSFERASE |
| Fe | IRON |
| Li | LITHIUM |
| ECO2 | CARBON DIOXIDE (ENZYMATIC METHOD) |
| LDH | LACTATE DEHYDROGENASE |
| GGT | GAMMA GLUTAMYL TRANSFERASE |
| ALC | ALCOHOL |
| DGXN | DIGOXIN |
| NH3/AMON | AMMONIA |
| PHYT | PHENYTOIN |
| CHOL | CHOLESTEROL |
| ACP | ACID PHOSPHATASE |
| PROT | CSF PROTEIN |
| SALI | SALICYLATE |
| CHE | CHOLINSTERASE |
| CREA | CREATININE |
| TP | TOTAL PROTEIN |
| TRIG | TRIGLYCERIDES |
| GLU | GLUCOSE |

A slide present signal is available at line 22a which is at 5V when a dry slide is present. This voltage drops to 2.5 V for a wet slide.

In summary, as a slide S enters the analysis station, a signal on the line 60a goes from approximately 0 volts to approximately 12 volts thereupon producing a slide present signal on the order of 5 volts for a dry slide on the output line 22a. At the same time, the voltage on the line 62a goes from approximately 0 volts to about 10 volts in the presence of a dry slide S. Similarly, the output voltage on the line 64a goes from approximately 0 volts without a slide in the analysis station to about 10 volts in the presence of a dry slide. At this time, the voltage on the output signal line 22b is on the order of 50-55 mV.

When a spotting or wetness event takes place, the output signal on the line 62b drops on the order of 300 mV (or more). This in turn causes the output on the line 64a to drop to about 0 volts. The feedback Schottky diode CR3 then conducts thereby holding the positive input to amplifier 64a low, on the order of 200 mV which in turn causes the output on the line 64 to stay low, irrespective of the evaporative characteristics of the fluid F on the slide S.

Figure 6:
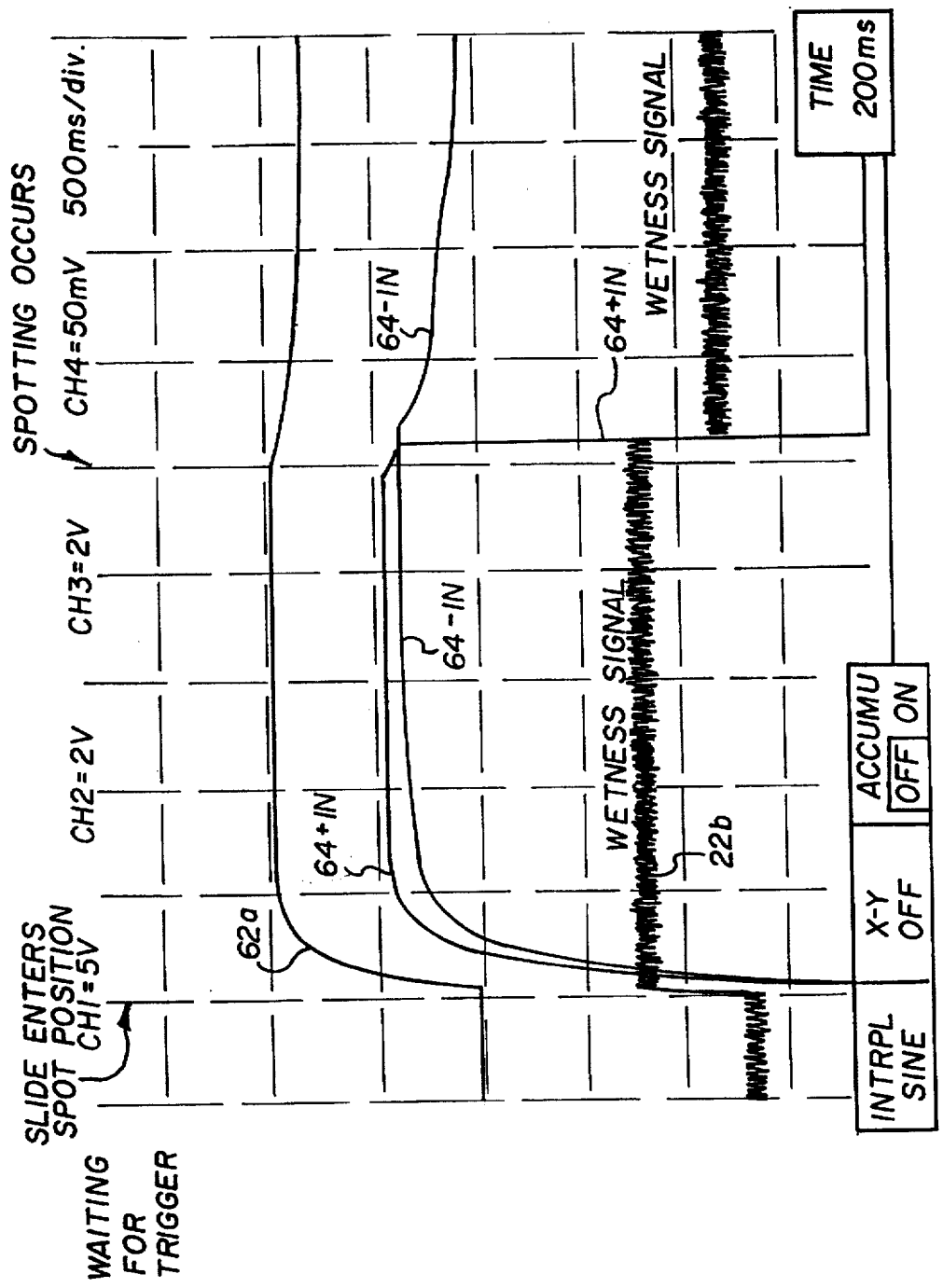
FIGS. 6 is a plurality of graphs illustrating performance of the system of FIG. 3.

A low signal on the line 64a in turn causes the signal on the line 22b to go low to about 10 mV indicating the wetness or spotting event. This process is illustrated in the graphs of FIG. 6.

Schottky diode CR4 enables the circuitry to recover between slides in about 0.5 sec. If a standard silicon diode is used, about 3 seconds are needed.

From the foregoing, it will be observed that numerous variations and modifications may be effected without departing from the spirit and scope of the invention. It is to be understood that no limitation with respect to the specific apparatus illustrated herein in tended or should be inferred. It is, of course, intended to cover by the appended claims all such modification as fall within the scope of the claims.

What is claimed is:

1. A circuit for detecting wetting of a test element using a light emitting diode and photodiode positioned to detect light from the test element by reflectance only, the circuit comprising:

an amplifier to amplify a change in detected light reflectance wherein said amplifier has a first dynamic range and wherein said amplifier includes limiter circuitry to limit said change in detected light reflectance thereby producing a second, larger, dynamic range for said amplifier; and a conditioning circuit disposed to receive an output from said amplifier, wherein said circuit includes a capacitor, a voltage comparator and at least one diode effective to charge the capacitor at a first rate in response to the initial presence of a test element and then at a second, lower, rate.

2. A circuit as in claim 1 which includes:

a resistor coupled to said capacitor to maintain a charge on said capacitor.

3. A circuit as in claim 1 which includes a current-to-voltage converter coupled between the photodiode and said amplifier.

4. A circuit as in claim 1 which includes comparator circuitry coupled to the photodiode for generating a signal indicative of the presence of the test element.

5. A circuit as in claim 1 wherein said conditioning circuit includes a comparator and a non-linear feedback element wherein when said comparator switches from a first state to a second state, said feedback element conducts and maintains said second state.

6. A reflective detector of a wetting event on a region of a test medium, the detector comprising:

a solid state source of a beam of radiant energy wherein said beam is incident on the region at an angle less than ninety degrees;

a solid state sensor of radiant energy reflected from the region wherein said sensor is oriented normal to at least a part of the region and wherein said sensor generates on electrical signal indicative of the detected, reflected, radiant energy; and an amplifier circuit coupled to said sensor wherein said amplifier has a first dynamic range and includes circuitry for expanding said first dynamic range to a second, greater, dynamic range.

7. A detector as in claim 6 which includes comparator circuitry, coupled to said amplifier circuit, for comparing a signal from said amplifier to a variable threshold wherein said threshold changes at first and second, different, rates.

8. A detector as in claim 7 which includes a non-linear feedback element coupled to said comparator for clamping a comparator input signal to a first state in response to a predetermined output from said comparator.

9. A detector as in claim 6 which includes a housing wherein said housing defines an internal, substantially closed, region wherein said sensor is located on said normal, in said region displaced a predetermined distance from the wetted region.

10. A detector as in claim 6 which includes circuitry for generating a signal indicative of the presence of the test medium.

11. A detector as in claim 6 which includes a conditioning circuit, coupled to said amplifier circuit, wherein said conditioning circuit generates a threshold voltage which has a first rate of change in response to a first condition and a second, lower, rate of change in response to a different condition.

12. A reflective apparatus for detecting a wetting event on a region of a test medium comprising:

a hollow housing having first and second ends and defining an internal channel therebetween wherein said channel extends substantially perpendicular to the medium with one end closer to the medium than the other;

a sensor coupled to said other end;

a solid state source of radiant energy, oriented at an acute angle relative to the medium and on the same side thereof as said housing;

conditioning circuitry for detecting a wetting event on the medium, indicated by a drop in reflected radiant energy wherein said circuitry includes threshold establishing circuitry with first and second establishing rates.

13. An apparatus as in claim 12 which includes a comparator having first and second inputs and an output wherein one of said inputs is coupled to said threshold establishing circuitry.

14. An apparatus as in claim 13 which includes a non-linear feedback element coupled between said output and said other input.

15. A media analysis system comprising:

a media transport unit;

an injection unit for depositing a wetting fluid on a portion of a medium being analyzed;

a solid state source of radiant energy for directing a beam of radiant energy toward the medium at an acute angle;

a solid state sensor of radiant energy reflect from the medium wherein said sensor is perpendicular to a line normal to the medium; and conditioning circuitry, coupled to said sensor, wherein said circuitry includes a comparator for comparing a signal indicative of reflected radiant energy to a variable threshold value wherein said value is established at first and second rates wherein said rates are different.

16. A method of detecting a wetting event on a medium comprising:

directing radiant energy toward an analysis location;

moving a medium to the location;

detecting radiant energy reflected from the medium along a line normal to the medium;

establishing a variable threshold value as the medium is moved to the location wherein the value is established, in part, at a first rate as the medium is moved to the location and at a second, lower rate, when the medium is at the location;

producing a signal indicative of reflected radiant energy when the medium is at the location:

depositing a fluid into at least a portion of the medium;

comparing the signal to the variable threshold, and, in response to a drop in reflected radiant energy due to said deposited fluid, generating an output, wetting event indicating signal.

* * * * *